United States Patent [19]

Valone

[11] Patent Number: 4,647,589

[45] Date of Patent: Mar. 3, 1987

[54] INHIBITION OF MICROBIOLOGICAL GROWTH

[75] Inventor: Frederick W. Valone, Houston, Tex.

[73] Assignee: Texaco Inc., White Plains, N.Y.

[21] Appl. No.: 614,002

[22] Filed: May 25, 1984

[51] Int. Cl.[4] .......................................... A01N 37/18
[52] U.S. Cl. ................................... 514/627; 514/617; 514/623; 514/624; 514/625; 514/613
[58] Field of Search ............... 564/204; 424/320, 324; 514/613, 624, 617, 625, 623, 627

[56] References Cited

U.S. PATENT DOCUMENTS 3,878,247 4/1975 Moss et al. .................... 564/204

OTHER PUBLICATIONS

Cationic Monomers: DMAPMA, MAPTAC; Virginia Chemicals, pp. 1-16.

Technical Bulletin: Cationic Monomers, Jefferson Chemical Company, pp. 1-10; Mar. 1976.

*Primary Examiner*—Leonard Schenkman
*Assistant Examiner*—Joseph A. Lipovsky
*Attorney, Agent, or Firm*—Robert A. Kulason; James J. O'Loughlin; Carl G. Seutter

[57] ABSTRACT

Aqueous substrates are treated to inhibit microbiological growth by addition of dimethylaminopropylmethacrylamide or dimethylaminopropylacrylamide.

In the presence of corrosion inhibitors, it is found that the instant biocides will permit attainment of 100% biocidal kill when present in lesser amounts than are required when no corrosion inhibitor is present. Presence of the instant biocides causes no deletrious impact upon the corrosion inhibitors; and in fact an improvement in corrosion inhibition is observed in the presence of the biocide.

19 Claims, No Drawings

INHIBITION OF MICROBIOLOGICAL GROWTH

FIELD OF THE INVENTION

This invention relates to the inhibition of microbiological growth. More particularly it relates to a system particularly characterized by its ability to inhibit growth of sulfate-reducing bacterial.

BACKGROUND OF THE INVENTION

As is well-known to those skilled in-the-art, the presence of microbiological contaminants in liquid systems causes undesirable problems typified by increased corrosion rates and plugging of conduits, filters, pumps, etc. During petroleum production, it is found that a particular source of problems is the presence of sulfate reducing bacteria "SRB", in aqueous systems including those containing both a hydrocarbon phase and an aqueous phase. Sulfate-reducing bacteria, such as clostridia nigrificans, or Desulfovibro are a particular problem due to their ability to metabolize inorganic sulfate to sulfide.

A wide variety of bacteriocides have heretofore been employed in various environments. Typical of those proposed as disinfectants for skin or hard surfaces is $H_2C=CRCONH(C_6H_4)XY$ wherein X and Y are —Cl, —NO$_2$ or —OH. See Linfield et al J. Med. Chem. 1983 26, 1741–1746.

It is an object of this invention to provide a process for inhibiting the growth of SRB in an aqueous system or in systems containing both hydrocarbon and aqueous phases. Other objects will be apparent to those skilled in the art.

STATEMENT OF THE INVENTION

In accordance with certain of its aspects, this invention is directed to a process of inhibiting microbiological growth in aqueous locus which comprises treating said locus with a microbiologically effective amount of, as biocidal additive,

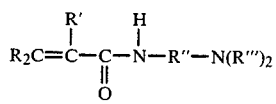

wherein R and R''' are hydrogen, alkyl, aralkyl, cycloalkyl, alkaryl, alkenyl, alkynyl, or aryl; R' is hydrogen, alkyl, aralkyl, cycloalkyl, alkaryl, or aryl; and R'' is alkylene, aralkylene, alkarylene, cycloalkylene, or arylene.

DESCRIPTION OF THE INVENTION

The microbiological inhibition system of this invention is found to be particularly effective in substrates which include an aqueous or an aqueous-hydrocarbon component typified by those found in petroleum production including liquids (aqueous or aqueous-hydrocarbon) found in subterranean well holes, in surface ponds or reservoirs of crude oil, in salt water separated from crude oils, and on the various metal equipment which come into contact with these fluids, typified by pipes, tanks, pumps, structural members, etc.

Although undesirable microbiological growth may include fungi, gram-positive bacteria, and gram-negative bacteria, a particularly undesirable source of problems is the sulfate-reducing bacteria. These SRB are undesirable because of their ability to produce inorganic sulfide during sulfate-ion metabolism.

It is a feature of the process of this invention that it may be possible to inhibit (and in many instances totally destroy all) these bacteria and particularly the SRB by addition to the substrate (aqueous or aqueous-hydrocarbon) of a microbiologically effective amount of

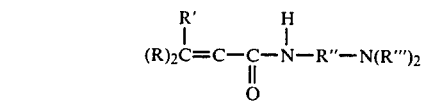

wherein R and R''' are hydrogen, alkyl, aralkyl, cycloalkyl, alkaryl, alkenyl, alkynyl, or aryl; R' is hydrogen, alkyl, aralkyl, cycloalkyl, alkaryl, or aryl; and R'' is alkylene, cycloalkylene, or arylene.

In the above formula. R may be hydrogen or a hydrocarbon radical selected from the group consisting of alkyl, aralkyl, cycloalkyl, aryl, alkaryl, alkenyl, and alkynyl including such radicals when inertly substituted. When R is alkyl, it may typically be methyl, ethyl, n-propyl, iso-propyl, n-butyl, i-butyl, sec-butyl, amyl, octyl, decyl, octadecyl, etc. When R is aralkyl, it may typically be benzyl, etc. When R is cycloalkyl, it may typically be cyclohexyl, cycloheptyl, 2-methylcycloheptyl, 3-butylcyclohexyl, 3-methylcyclohexyl, etc. When R is aryl, it may typically be phenyl, etc. When R is alkaryl, it may typically be tolyl, etc. When R is alkenyl, it may typically be vinyl, allyl, 1-butenyl, etc. When R is alkynyl, it may typically be ethynyl, propynyl, butynyl, etc. R may be inertly substituted i.e. it may bear a non-reactive substituent such as alkyl, aryl, cycloalkyl, ether, halogen, nitro, etc. Typically inertly substituted R groups may include 3-chloropropyl, 2-ethoxyethyl, carboethoxymethyl, 4-methylcyclohexyl, p-chlorophenyl, p-chlorobenzyl, 3-chloro-5-methylphenyl, etc. The preferred R group may be hydrogen or lower alkyl, i.e. $C_1$–$C_6$ alkyl, groups including e.g. methyl, ethyl, n-propyl, i-propyl, butyls, amyls, hexyls, etc. R may more preferably be hydrogen. Preferably both R groups are hydrogen.

R' may be hydrogen or alkyl, aralkyl, cycloalkyl, alkaryl, or aryl hydrocarbon groups. These hydrocarbons may be selected from the same group as that from which R is selected. Preferably R' may be hydrogen or methyl.

It may be noted that generally less bulky molecules are believed to be more effective; and accordingly R is preferably hydrogen and R' is preferably hydrogen or —CH$_3$.

R''' may be selected from the same group as that from which R is selected. Preferably R''' maybe methyl; and preferably both R''' groups are methyl.

In the above formula, R'' may be a hydrocarbon group selected from the group consisting of alkylene, aralkylene, cycloalkylene, arylene, and alkarylene, including such radicals when inertly substituted. When R'' is alkylene, it may typically be methylene, ethylene, n-propylene, iso-propylene, n-butylene, i-butylene, sec-butylene, amylene, octylene, decylene, octadecylene, etc. When R'' is aralkylene, it may typically be benzylene, beta-phenylethylene, etc. When R'' is cycloalkylene, it may typically be cyclohexylene, cycloheptylene, cyclooctylene, 2-methylcycloheptylene, 3-butylcyclohexylene, 3-methylcyclohexylene, etc. When R'' is arylene, it may typically be phenylene, naphthylene, etc. When R" is alkarylene, it may typically be tolylene, xylylene, etc. R" may be inertly substituted i.e. it may bear a non-reactive substituent such as alkyl, aryl, cycloalkyl, ether, halogen, nitro, etc. Typically inertly substituted R" groups may include 3-chloropropylene, 2-ethoxyethylene, carboethoxymethylene, 4-methylcyclohexylene, p-chlorophenylene, p-chlorobenzylene, 3-chloro-5-methylphenylene, etc. The preferred R" groups may be lower alkylene, i.e. $C_1$–$C_{10}$ alkylene, groups including e.g. methylene, ethylene, n-propylene, i-propylene, butylene, amylene, hexylene, octylene, decylene, etc. R" may preferably be a polymethylene group —$(CH_2)_n$— wherein n is a small integer 1–10, say 3; and preferably R" is propylene-$CH_2CH_2CH_2$—.

The preferred biocide compounds

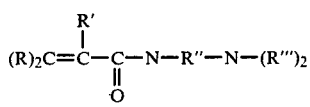

which may be used in practice of the process of this invention may typically include those listed in the following table, the first listed being preferred:

TABLE I

| Designation | Biocide |
|---|---|
| I - A | $CH_2{=}\underset{\underset{O}{\|}}{C}{-}\underset{CH_3}{\overset{\|}{C}}{-}\underset{H}{\overset{\|}{N}}(CH_2)_3N(CH_3)_2$ |
| I - B | $CH_2{=}CH{-}\underset{\underset{O}{\|}}{C}{-}\underset{H}{\overset{\|}{N}}(CH_2)_3N(CH_3)_2$ |
| I - C | $CH_2{=}CH{-}\underset{\underset{O}{\|}}{C}{-}\underset{H}{\overset{\|}{N}}(CH_2)_3N(C_2H_5)_2$ |
| I - D | $CH_2{=}CH{-}\underset{\underset{O}{\|}}{C}{-}\underset{H}{\overset{\|}{N}}(CH_2)_3NHCH_3$ |
| I - E | $CH_2{=}CH{-}\underset{\underset{O}{\|}}{C}{-}\underset{H}{\overset{\|}{N}}(CH_2)_2NHCH_3$ |

These compounds are commercially available or may be readily prepared by known methods. The first listed compound is available from Texaco Chemical Company under the trademark DMAPMA and the second listed is marketed under the trademark DMAPAA.

Practice of this aspect of the invention may be carried out by addition to the system of a microbiologically effective amount of the biocide. Typically the desired results may be obtained by the presence of 5–1000 ppm, preferably 5–50, say about 15 ppm of biocide based on the aqueous substrate. Lesser amounts may be employed but the results will be less satisfactory. Larger amounts may be employed without deleterious effort, but this is generally less economical and usually unnecessary.

In practice, the biocidal additive may be added to the aqueous or aqueous-hydrocarbon substrate in which it is desired to inhibit microbiological growth and particularly growth of SRB. This may be done continuously or intermittently. The additive may be added to an aqueous medium (containing other ingredients) which is to be pumped into an oil well. It may be added to aqueous medium recovered from the well as in the case of crude petroleum. It may be added to the crude petroleum before separation of aqueous liquids. For ease of handling, the biocide may be employed as a concentrate, preferably in diluent-solvent such as water, alcohol, etc; and this may be added to the substrate in amount sufficient to form the desired operating concentration. (containing 1–30 w%, say 10 w% of active ingredient).

It is found that the so formulated compositions are particularly resistant to growth of SRB; and use of these compositions, containing additive in amounts as small as 5 ppm, may be sufficient to effectively control SRB.

Preliminary screening of these compositions against sulfate-reducing bacteria which cause undesirable problems in oil field technology may be carried out by the Standard Biocide Test, described in the American Petroleum Institute Standard Practice, RP 38 (First Edition, May 1959).

Illustrative compositions may be formulated as follows:

(i) 15 ppm (vol) of the DMAPMA brand of dimethylaminopropylmethacrylamide may be added to a water-injection well to permit secondary oil recovery to be carried out;

(ii) 15 ppm (vol) of the DMAPAA brand of dimethylaminopropylacrylamide may be added to salt water separated from crude petroleum;

(iii) 15 ppm (vol) of the DMAPMA brand of dimethylaminopropylmethacrylamide may be added to crude petroleum prior to desalting; etc.

(iv) 15 ppm (vol) of the DMAPMA brand of dimethylaminopropylmethacrylamide to crude petroliferous fluids prior to surface handling (e.g. gas removal, water separation, etc.)

It is a feature of the biocides of this invention that they may be used in combination with corrosion-inhibitors whether water-soluble or hydrocarbon-soluble. Illustrative corrosion inhibitors which may be employed may include:

TABLE II

| Description | Corrosion Inhibitor |
|---|---|
| II - A | A particularly useful water-soluble corrosion inhibitor may be typically prepared by the reaction of (i) an amine mixture containing a poly (oxyethylene) diamine $M_n$ 500–700 and a poly (oxypropylene) triamine $M_n$ 300–500, in mole ratio of 0.8–1.25 with (ii) an organic monomer acid mixture containing a petrolatum oxidate and a fatty acid in mole ratio of 0.8–1.25:1. Reaction is typically carried out at elevated temperature of typically 160° C. for 0.5–10 hours, say 2 hours. After heating, there is added an inert solvent (typically 1:1 isopropyl alcohol/water). This corrosion inhibitor is particularly effective in sour aqueous systems. |
| II - B | The Petrolite KP-203 brand of inhibitor containing a cyclohexanone ammonium nitrate salt and a dinonylphenol surfactant. |
| II - C | The Nalco Visco 4977 brand of inhibitor containing an oil-soluble, slightly |

TABLE II-continued

| Description | Corrosion Inhibitor |
|---|---|
|  | water-dispersible amine salt of a fatty acid. |
| II - D | A corrosion inhibitor containing: |
|  | 12.2 v % of 1-aminoethyl-2-glyoxaldine, |
|  | 15.2 v % of polymerized fatty acids containing 80% dimer and 20% trimer acid |
|  | 0.8 v % of poly-oxyethylene (23) lauryl alcohol |
|  | 71.8 v % of aromatic solvent |

Practice of one preferred embodiment of the process of this invention may be carried out by adding both biocide and corrosion inhibitor to the aqueous or aqueous hydrocarbon system. Preferably the biocide may be present in microbiologically effective amount, typically in amount of 5-1000 ppm, typically 5-50, say about 15 ppm (vol); and the corrosion inhibitor may be present in corrosion inhibiting amount, typically in amount of 10-1000 ppm, preferably 25-250 ppm, say 150 ppm, (vol). In the preferred embodiment, the volume ratio of biocide to corrosion inhibitor may be 1-10:1, preferably 6-8:1, say ca. 7:1. One preferred embodiment may contain 20 ppm biocide and 150 ppm corrosion inhibitor.

STANDARD CORROSION TEST

Details of this test are disclosed in the January 1968 issue (pages 34-35) of *Materials Protection*.

In this test, metal specimens were immersed in sour fluid environments for seventy-two (72) hours to approximate continuous exposure conditions in the oil field. A sour fluid test environment was created by bubbling hydrogen sulfide throught the test solution. Tests were additionally run in this environment without any organic corrosion inhibitors placed in the test solutions to give a baseline for comparison purposes.

The metal test specimens were cold-rolled, mild steel coupons which measured 3 inches by 0.5 inches by 0.005 inches. These coupons were initially cleaned in order to remove any surface film, dried, and then weighed.

Four ounce glass bottles were filled with two types of test solutions. The first simulated an oil-brine environment and consisted of 10 milliliters of Texaco EDM brand fluid, a lube oil cut having an API gravity of about 39°, and 90 milliliters of a 10% synthetic brine, and 1 milliliter of dilute acetic acid. The synthetic brine contained 10% sodium chloride and 0.5% calcium chloride by weight. The second test solution simulated a brine environment and was composed of 100 milliliters of the same 10% synthetic brine and 1 milliliter of dilute acetic acid. The oil-brine and brine test solutions were then gassed for 5 to 10 minutes with hydrogen sulfide to create a sour test environment. The solution gassing was designed to remove any dissolved oxygen as well as create the sweet or sour environment.

Next, 10-1000 (preferably 125-175) parts per million of a selected organic corrosion inhibitor were added to the gassed bottles. Each inhibitor addition was made from a standard solution of known concentration.

The steel test coupons were then placed in the bottles. The bottles were capped and mounted on the spokes of a 23 inch diameter, vertically mounted wheel and rotated for 72 hours at 30 rpm inside an oven maintained at 120° F. (49° C.). The coupons were removed from the bottles, washed, scrubbed with an abrasive cleaner, dried and weighed. The corrosion rate in mils per year (mpy) was then calculated from the weight loss. One mpy is equivalent to 0.001 inches of metal lost per year to corrosion. Additionally, the test coupons were visually inspected for the type of corrosive attack, e.g., hydrogen blistering, pitting and crevice corrosion, or general corrosion.

It is found that practice of this invention permits attainment of outstanding results. The novel biocide is found to be effective to reduce the concentration of sulfate reducing bacteria under field conditions. It is possible to lower the concentration of sulfate-reducing bacteria SRB by use of the novel biocides in aqueous or aqueous hydrocarbon systems in concentrations as low as e.g. 15 parts per million.

It is also unexpectedly found that the combination of the novel biocides and corrosion inhibitors permits attainment of outstanding results. Presence of the biocide is found to have no deletious effect on the corrosion inhibitor. Typically presence of the corrosion inhibitor unexpectedly permits outstanding biocidal results to be attained with lesser quantities of biocide. For example it is found that, in the presence of 5-10 ppm (vol) of corrosion inhibitor IIA of the Table II supra, it is possible to kill all SRB by use of as little as 5-10 ppm (vol) of biocide.

In the absence of corrosion inhibitor, it may be necessary to use as much as 10-15 ppm biocide to attain a comparable kill level.

Practice of the process of this invention will be apparent to those skilled in the art from the following wherein, as elsewhere in this application, all parts are parts by weight unless otherwise specified.

DESCRIPTION OF THE PREFERRED EMBODIMENT

Example I

In this example which represents the best mode presently known of practicing the process of this invention, the DMAPMA brand of dimethylaminopropylmethacrylamide biocide is tested for its biocidal activity by the Standard Biocidal Test supra. The biocide is added in the amount designated and the effectiveness is measured.

TABLE

| Concentration ppm (vol) | Effectiveness |
|---|---|
| 10 | 100% |
| 15 | 100% |
| 25 | 100% |
| 50 | 100% |
| 100 | 100% |
| 500 | 100% |

From these data, it is apparent that DMAPMA is an extremely effective biocide at very low concentrations.

Example II

In this example, the biocide is the DMAPAA brand of dimethylaminopropylacrylamide. The results are as follows:

TABLE

| Concentration ppm (vol) | Effectiveness |
|---|---|
| 10 | 100% |
| 15 | 100% |
| 25 | 100% |
| 50 | 100% |

| Concentration ppm (vol) | Effectiveness |
|---|---|
| 100 | 100% |
| 500 | 100% |

From these data, it is apparent that the DMAPAA brand of product is effective.

Example III*

In this control example, the biocide employed is a quaternary compound—methacrylamidopropyl trimethyl ammonium chloride (falling outside the scope of this invention).

| Concentration ppm (vol) | Effectiveness |
|---|---|
| 10 | 0% |
| 15 | 0% |
| 25 | 0% |
| 50 | 0% |
| 100 | 0% |
| 500 | 0% |

From these data, it is apparent that the quaternary ammonium chloride salt of DMAPMA is not effective against sulfate reducing bacteria.

Results comparable to those of Example I may be attained if the biocide is

| Example | Biocide |
|---|---|
| IV | -Magnacide B brand of acrolein |
| V | -Tretolite XC-102, brand of aldehyde bactericide |
| VI | -Tretolite XC-401 brand of blend of bactericidal diamines and polychlorinated Phenolic compounds |
| VII | -Nalco Visco 1153 brand of cationic surface-active biocide |

Example VIII*

In this control example, the compositions tested contained corrosion inhibitor. The corrosion inhibitor IIA of Table II is prepared by reacting:

(i) the Jeffamine ED-600 brand of poly (oxyethylene) diamine $\overline{M}_n$ 600

wherein a+c is about 3.5 and b is about 13.5;

(ii) the Jeffamine T-403 brand of poly (oxypropylene) triamine $\overline{M}_n$ 400

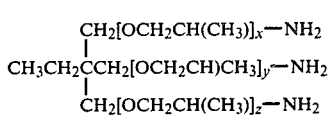

wherein x+y+z is 5.3

(iii) the Texaco TC-5926 brand of petrolatum oxidate prepared by oxidizing a hydrocarbon lubricating oil to form a product of molecular weight of about $\overline{M}_n$ 350 and containing principally mono-acid. Sap No. is 310. Neut. No. is 160; and (iv) the Hercules Pamak WCFA brand of tall oil derived fatty acid containing 11% rosin acid, 8% unsaponifiables, and having a Garner Color of 8, an Acid Number of 178, an Iodine Number of 133, and a Titer of 3° C.

The corrosion inhibitor is made by adding these compounds to a reaction vessel in weight ratio of 5:5:2:2. The reaction mixture is heated for 3 hours at 160° C. The amide corrosion inhibitor so prepared is made up into a solution containing the following:

| Component | w % |
|---|---|
| 1. A 50 w % solution of isopropanol in water | 73 |
| 2. Corrosion Inhibitor supra | 25 |
| 3. The Texaco M-320 brand of poly (20) (oxyethylene) amine surfactant characterized as follows: | 2 |
| Amine Content (meg/g) 0.75 | |
| Hydroxyl Nol (mg KOH/g) 91 | |
| Moles of ethylene oxide 20 | |
| Sp. Gr. 20°/20° C. 1.0645 | |
| Pour Point, °F. 55° | |
| pH (1% solution) 9.65 | |

Example IX

In this example of practice of the process of this invention, a composition containing 5–15 ppm (vol) of the biocide of Example I and 150 ppm (vol) of the corrosion inhibitor of Example VIII is tested for corrosion inhibition and biocidal activity by the Standard Tests noted supra.

| Corrosion Inhibitor ppm | Biocide ppm | Biocide Necessary for 100% Kill | % Protection All Brine |
|---|---|---|---|
| 0 | 15 | 15 | — |
| 10 | 10 | 10 | — |
| 150 | 150 | — | 93 |
| 150 | 0 | — | 92 |

From the above, it is apparent that, in the presence of the biocide, the corrosion inhibition properties of the system are maintained; and the synergistic effect of the corrosion inhibition agent permits complete biocidal kill at a level of 10 ppm of biocide.

Results comparable to those of Example IX may be obtained if the biocide and the corrosion inhibitor are as follows:

| Example | Biocide | Corrosion Inhibitor |
|---|---|---|
| X | DMAPMA | The condensate of polymeric acid and 1-aminoalkyl-2-alkyl imadazoline of U.S. Pat. No. 3,623,979 |
| XI | DMAPMA | The Nalco Visco 4977 brand of inhibitor containing an oil-soluble, slightly water-dispersible amine salt of a fatty acid. |
| XII | DMAPMA | The Tretolite KP-203 brand of inhibitor containing a cyclohexanone-ammonium nitrate salt and a di-nonylphenol |

TABLE-continued

| Example | Biocide | Corrosion Inhibitor |
|---------|---------|---------------------|
|         |         | surfactant.         |

Although this invention has been illustrated by reference to specific embodiments, it will be apparent to those skilled in the art that various changes and modifications may be made which clearly fall within the scope of this invention.

What is claimed:

1. The process of inhibiting microbiological growth in a hydrocarbon or aqueous locus containing undesirable microbial growth which comprises treating said locus with a microbiologically effective amount of, as biocidal additive,

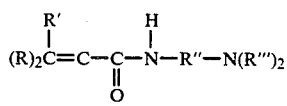

wherein R and R''' are hydrogen, alkyl, aralkyl, cycloalkyl, alkaryl, alkenyl, alkynyl, or aryl; R' is hydrogen, alkyl, aralkyl, cycloalkyl, alkaryl, or aryl; and R'' is alkylene, aralkylene, alkarylene, cycloalkylene, or arylene.

2. The process of inhibiting microbiological growth as claimed in claim 1 wherein R is hydrogen.

3. The process of inhibiting microbiological growth as claimed in claim 1 wherein R' is hydrogen.

4. The process of inhibiting microbiological growth as claimed in claim 1 wherein R' is methyl.

5. The process of inhibiting microbiological growth as claimed in claim 1 wherein R'' is polymethylene.

6. The process of inhibiting microbiological growth as claimed in claim 1 wherein R'' is —CH$_2$CH$_2$CH$_2$—.

7. The process of inhibiting microbiological growth as claimed in claim 1 wherein R''' is methyl.

8. The process of inhibiting microbiological growth as claimed in claim 1 wherein said biocidal additive is

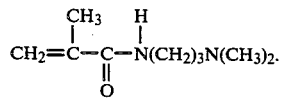

9. The process of inhibiting microbiological growth as claimed in claim 1 wherein said biocidal additive is

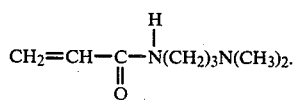

10. The process of inhibiting microbiological growth as claimed in claim 1 wherein said biocidal additive is present in concentration of 5–1000 ppm.

11. The process of inhibiting microbiological growth in an aqueous locus containing undesireable microbial growth which comprises treating said locus with 5–1000 ppm of, as a biocidal additive,

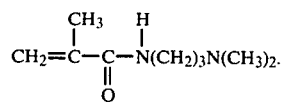

12. The process of inhibiting microbiological growth in a hydrocarbon or aqueous locus containing undesireable microbial growth which includes metal surfaces which are subject to corrosion which comprises treating said locus with corrosion inhibiting amount of a corrosion inhibiting additive and a microbiologically effective amount of, as biocidal additive

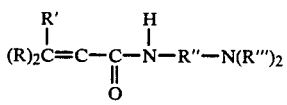

wherein R and R''' are hydrogen, alkyl, aralkyl, cycloalkyl, alkaryl, alkenyl, alkynyl, or aryl; R' is hydrogen, alkyl, aralkyl, cycloalkyl, alkaryl, or aryl; and R'' is alkylene, aralkylene, alkarylene, cycloalkylene, or arylene.

13. The process of inhibiting microbiological growth as claimed in claim 12 wherein R is hydrogen.

14. The process of inhibiting microbiological growth as claimed in claim 12 wherein R' is methyl.

15. The process of inhibiting microbiological growth as claimed in claim 12 wherein R'' is polymethylene.

16. The process of inhibiting microbiological growth as claimed in claim 12 wherein R'' is —CH$_2$CH$_2$CH$_2$—.

17. The process of inhibiting microbiological growth as claimed in claim 12 wherein R''' is methyl.

18. The process of inhibiting microbiological growth as claimed in claim 12 wherein said biocidal additive is

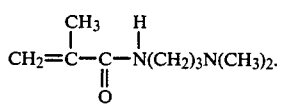

19. The process of inhibiting microbiological growth as claimed in claim 12 wherein said biocidal additive is

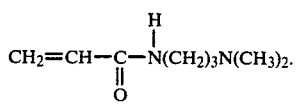

* * * * *